United States Patent
Gueret

(10) Patent No.: US 6,316,021 B1
(45) Date of Patent: Nov. 13, 2001

(54) EXTENSIBLE MASK INCLUDING AN ADHESIVE MATRIX THAT CAN BE STRETCHED AT LEAST IN THE WET STATE

(75) Inventor: Jean-Louis Gueret, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/534,025

(22) Filed: Mar. 24, 2000

(30) Foreign Application Priority Data

Apr. 1, 1999 (FR) .................................................. 99 04094

(51) Int. Cl.$^7$ ........................................................ A61K 9/70
(52) U.S. Cl. ..................... 424/443; 424/401; 424/402; 424/448; 424/487; 514/844
(58) Field of Search ............................... 424/443, 401, 424/70, 78, 402, 448, 487; 514/844

(56) References Cited

U.S. PATENT DOCUMENTS 5,026,552 * 6/1991 Gueret et al. .................... 424/401

FOREIGN PATENT DOCUMENTS

| | | |
|---|---|---|
| 0 309 309 A1 | 3/1989 | (EP) . |
| 2 538 247 A1 | 4/1984 | (FR) . |
| WO 96/14822 | 5/1996 | (WO) . |
| WO 97/32567 | 9/1997 | (WO) . |

OTHER PUBLICATIONS

Database WPI, Section Ch, Week 199412, Derwent Publications Ltd., London, GB; Class A96, AN 1994–097759, XP002125705.

* cited by examiner

Primary Examiner—Thurman K. Page
Assistant Examiner—Blessing Fubara
(74) Attorney, Agent, or Firm—Oliff & Berridge, PLC

(57) ABSTRACT

The invention relates to a mask for the face or the body, which mask comprises a backing sheet coated on one of its faces with an adhesive matrix containing a permanent adhesive that adheres both to dry skin and to wet skin, at least one of the backing sheet and the adhesive matrix containing at least one active ingredient serving to exert a specific action on the skin. The adhesive matrix is stretchable at least in the wet state, in order to enable the mask to be adapted to fit the shape of the face or of the portion of the body to be treated, the backing sheet being chosen to be capable, at least in the wet state, of stretching so as to accompany the deformations in the adhesive matrix.

33 Claims, 1 Drawing Sheet

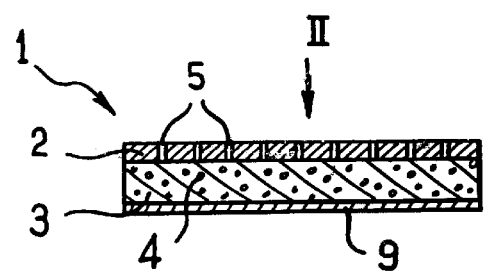
FIG_1
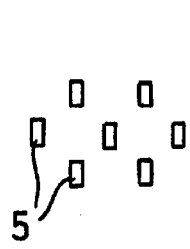
FIG_2
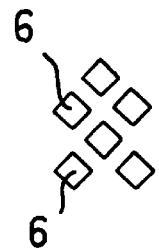
FIG_3
FIG_4
FIG_5
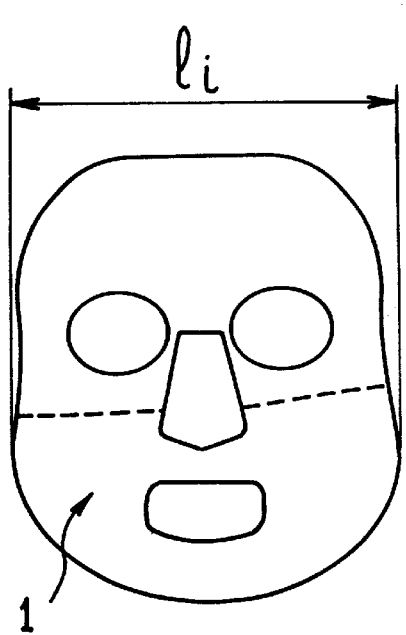
FIG_6
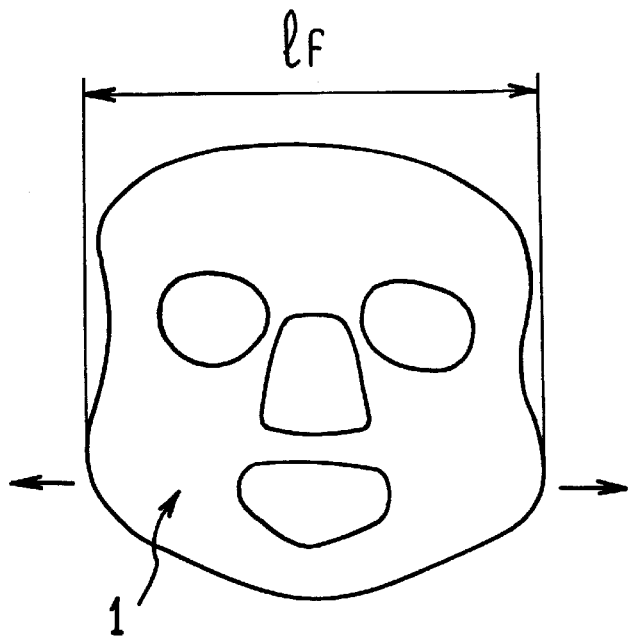
FIG_7

EXTENSIBLE MASK INCLUDING AN ADHESIVE MATRIX THAT CAN BE STRETCHED AT LEAST IN THE WET STATE

The present invention relates to a mask for the face or the body.

BACKGROUND OF THE INVENTION

A need exists to have a mask available than can easily be adapted to fit the morphology of the user, in particular in order to obtain more effective treatment.

OBJECTS AND SUMMARY OF THE INVENTION

An object of the invention is to propose a novel mask that is capable of being adapted easily to fit the various outlines and relief of the face or of the portion of the body over which it is applied.

The mask of the invention comprises a backing sheet coated on one of its faces with an adhesive matrix containing a permanent adhesive that adheres both to dry skin and to wet skin, at least one of the backing sheet and the adhesive matrix containing at least one active ingredient serving to exert a specific action on the skin, wherein the adhesive matrix is stretchable at least in the wet state, in order to enable the mask to be adapted to fit the shape of the face or of the portion of the body to be treated, the backing sheet being chosen to be capable, at least in the wet state, of stretching so as to accompany the deformations in the adhesive matrix.

By means of the invention, a mask is obtained that provides treatment that is more effective than the treatment provided by certain known masks that are not stretchable and that adhere to the skin only too weakly to enable them to be positioned properly while they are being applied.

In a particular embodiment, on being used, the mask has an elongation factor in at least one direction that lies in the range 5% to 30%, preferably in the range 10% to 30%, and more preferably in the range 15% to 30%.

Preferably, the adhesive is hydrophobic.

Also preferably, the adhesive matrix forms an occlusive layer.

The backing sheet may be provided with perforations and/or with cutouts serving to make it extensible or to increase its elongation factor.

For example, the perforations may be diamond-shaped.

For example, the cutouts may be in form of slots disposed in staggered manner.

Also in a particular embodiment, the adhesive matrix contains one or more water-absorbant substances, e.g. polyacrylates, natural or synthetic water-absorbant fibers or particles, alginates, and derivatives of corn [maize] or of cellulose.

In a particular embodiment, the adhesive matrix contains one or more active ingredients that are water-soluble and/or liposoluble.

The adhesive matrix may contain collagen.

The adhesive matrix and/or the backing sheet may contain dry extracts of animal or vegetable origin, and/or mineral substances.

Also in a particular embodiment, the backing sheet is made of a material that swells in water.

The backing sheet may be constituted by an elastic woven fabric.

In a variant, the backing sheet may be constituted by a hydrophilic non-woven fabric.

The backing sheet may contain one or more water-absorbant fibers or particles or substances, e.g. polyacrylates and/or a large proportion of viscose or of cotton, e.g. in the range 30% by weight to 90% by weight.

The backing sheet may contain polypropylene or polyester, e.g. in a proportion (by weight) lying in the range 5% to 95%.

In a particular embodiment, the mask contains active ingredients chosen to exert an action chosen from the following list: moistening, smoothing, lightening, toning up, slimming, healing, and anesthetizing.

In a particular embodiment, the adhesive and the backing sheet are chosen such that, once it is wet, the mask has a surface area in the stretched state that is greater by in the range 5% to 70% than the area of the mask in the dry state, and preferably greater by in the range 10% to 70%, and more preferably greater by in the range 20% to 70%.

The adhesive may be chosen from the following list: adhesives based on acrylic, vinyl, poylurethane, silicone, or elastomer (e.g. butyl or latex), and copolymers and/or mixtures thereof.

Advantageously, the adhesive matrix is chosen such that, when it is applied in the runny state on the backing sheet during manufacture of the mask, it has viscosity preventing it from passing through said backing sheet.

The adhesive matrix may contain plasticizers, oils or polyols (e.g. glycerine) in order to make it sufficiently stretchable.

The backing sheet and/or the adhesive matrix may be colored.

In a particular embodiment, the backing sheet is not stretchable so long as it is not impregnated with water, and preferably it is not stretchable when it is in contact with the matrix in the runny state, in solvent phase, during manufacture of the mask.

The invention also provides the use of a mask as defined above for treating the face, the neck, or the thighs, for example, the mask being immersed in water before it is applied, and then being applied to the preferably pre-wetted skin by being stretched so as to be adapted to fit the morphology of the user, or, in a variant, said mask is applied in the dry state on wet skin, and the backing sheet is then sprayed with water.

BRIEF DESCRIPTION OF THE DRAWING

The invention will be better understood on reading the following detailed description of non-limiting embodiments of the invention with reference to the accompanying drawing, in which:

FIG. 1 is a very diagrammatic section view showing the structure of an embodiment of a mask of the invention;

FIGS. 2 to 5 show various variants of perforations or cutouts provided in the backing sheet to make it easier for it to be deformed; and FIGS. 6 and 7 show the mask respectively in the initial state and in the stretched state.

MORE DETAILED DESCRIPTION

In the embodiment shown in FIG. 1, the mask comprises a backing sheet 2 coated on one face with an adhesive matrix 3 containing an adhesive and active ingredients 4 embedded in the adhesive.

A removable protective film 9 protects the adhesive matrix 3 before it is used.

The backing sheet 2 is provided with perforations 5 having a substantially rectangular shape as seen from above, as shown in FIG. 2.

In the example described, the backing sheet 2 is constituted by a non-woven fabric that swells in water and that is of density lying in the range 20 g/m² to 100 g/m², e.g. 50 g/m², including 30% of polyester fibers and 70% of viscose fibers.

In this example, the adhesive is a permanent adhesive based on acrylic.

Among other usable adhesives, mention can be made in particular of adhesives based on vinyl (e.g. vinyl acetate), polyurethane, silicone, or elastomer (e.g. butyl or latex), it being possible for the adhesives used to be partially cross-linked.

While the mask is being manufactured, the adhesive matrix 3 is coated in the runny state in a solvent phase on the backing sheet, its viscosity being high enough to prevent it from passing through the backing sheet.

In general, the adhesive matrix 3 is deposited in a quantity preferably lying in the range 15 g/m² to 70 g/M², and it preferably has a tackiness adhesive coefficient lying in the range 200 g/cm² to 600 g/cM² on dry skin and in the range 20 g/cm² to 150 g/cm² on wet skin.

In the example described, the adhesive matrix is deposited with a quantity of 40 g/m² and it constitutes an occlusive layer.

The above-described mask is not stretchable in the dry state because the backing sheet 2 is not stretchable in the dry state.

The mask is cut out to the shape of the portion of the body to be treated, and, where applicable, it is provided with cutouts for the eyes, the nose, and the mouth. Optionally, the mask is in two portions, the borderline between them being represented by a dashed line in FIG. 6.

In order to use the mask, the user immerses it in water, and then applies it to the skin, after having first wetted said skin. In a variant, the mask may be applied in the dry state on wet skin, the backing sheet then being sprayed with water.

The backing sheet 2, as filled with water, swells and spreads, thereby enabling the adhesive matrix 3 to be stretched by the user. In the example described, the elongation factor of a rectangle of a few cm² cut out in the mask is about 15% in the longitudinal direction.

The user starts by positioning one edge of the mask on the skin, and then gradually fits it to the entire surface to be treated.

The properties of the adhesive matrix make it possible to reposition the mask.

By means of the stretchability of the backing sheet and of the adhesive matrix, the mask can be adapted to fit the morphology of the user as well as possible.

The entire surface of the adhesive matrix 3 can thus come into contact with the entire face or the entire portion of the body to be treated.

By way of example, FIG. 7 shows the shape of the mask 1 once it has been stretched to fit the relief and outline of the face of the user.

By way of indication, in the example described, the initial width of the mask is approximately $l_i$=5 cm in the dry state and it goes to $l_r$=18 cm in the wet and stretched state.

The backing sheet 2 may be made in various manners without going beyond the ambit of the present invention.

It may be without any perforation, cell, or cutout, but rather it may merely be made of a material that swells in water and that is capable, once impregnated with water, of accompanying the deformations of the adhesive matrix on applying the mask to the face.

It is also possible for the backing sheet to be provided with any types of perforation or cell that enable its extensibility to be increased, e.g. diamond-shaped perforations 6, as shown in FIG. 3.

The backing sheet 2 may also be provided with slots disposed in staggered manner enabling the mask to stretch in a direction perpendicular to the slots, by means of the edges of the slots moving apart, in the manner of an expanded metal.

The backing sheet 2 may also be provided with Z-shaped cutouts 8 disposed in staggered manner, as shown in FIG. 5. The edges of these cutouts can move apart when the mask is stretched.

All types of active ingredients 4 may be incorporated into the adhesive matrix 3 and/or into the backing sheet 2, as a function of the treatment that is to be performed.

The adhesive matrix 3 may in particular include particles capable of absorbing moisture, so as to pump water into the adhesive matrix 3 and so as to facilitate solubilizing hydrophilic active ingredients serving to exert a determined effect on the skin.

Among the active ingredients used, mention may be made of anti-oxidant cleansing agents, free radical scavengers, moisturizers, depigmenting agents, liporegulators, anti-acne agents, antidandruff agents, anti-aging agents, softeners, antiwrinkle agents, keratolitic agents, anti-inflammatory agents, fresheners, healing agents, vascular protectors, antibacterial agents, antifungal agents, antiperspirants, deodorants, skin conditioners, anesthetics, immunomodulators, nourishing agents, and sebum absorbers (e.g. Orgasol) or moisture absorbers.

The adhesive matrix 3 may thus include a water-soluble active ingredient chosen from the following compounds: ascorbic acid and its biologically-compatible salts, enzymes, antibiotics, tightening agents, α-hydroxy acids and their salts, hydroxylated polyacids, sucroses and their derivatives, urea, aminoacids, oligopeptides, water-soluble plant extracts and yeast extracts, protein hydrolysates, hyaluronic acid, mucopolysaccharides, vitamins $B_2$, $B_6$, H, PP, panthenol, folic acid, salicylic acetyl acid, allantoin, glycyrrhetic acid, kojic acid, and hydroquinone.

The adhesive matrix 3 may further include at least one liposoluble active ingredient chosen from the following compounds: d-α-tocopherol, dl-α-tocopherol, dα-tocopherol, dl-α-tocopherol acetate, ascorbyl palmitate, vitamin F and glycerides of vitamin F, vitamin D, vitamin $D_2$, vitamin $D_3$, retinol, retinol esters, retinol palmitate, retinol propionate, β-carotene, d-panthenol, farnesol, farnesyl acetate; jojoba oils and black-currant oils rich in essential fatty acids; keratolytics such as salicylic acid, its salts and its esters, n-octanoyl-5 salicylic acid and its esters, α-hydroxyacid alkylesters such as citric acid, lactic acid, glycolic acid, asiatic acid, madecassic acid, asiaticoside, total extract of centella asiatica, β-glycyerrhetinic acid, α-bisabolol, ceramides such as 2 oleoylamino-1,3 octadecane; phytanetriol, milk sphingomyelin, phospholipids of marine origin rich in polyunsaturated essential fatty acids, ethoxyquin; rosemary extract, melissa extract, quercetin, extract of dried microalgae, and steroid anti-inflammatory agents.

Such active ingredients may be incorporated in the solubilized state into oils used alone or in association, among which mention can be made of the following: oils of animal, vegetable, or mineral origin, and in particular animal or vegetable oils formed by esters of fatty acids and of polyols, in particular liquid triglycerides, e.g. sunflower, corn, soya, vegetable marrow, sesame, hazelnut, pistachio nut, apricot, almond, or avocado oils; fish oils, glycerol tricaproccaprylate, or vegetable or animal oils of formula $R_1COOR_2$ in which $R_1$ represents the remainder of a higher fatty acid having from 7 to 19 carbon atoms, and $R_2$ represents a branched hydrocarbonated chain containing from 3 to 20 carbon atoms, e.g. Purcellin oil; wheat germ, calophyllum, sesame, coriander, and safflower oils, passion flower oil, rosa mosqueta oil, macadamia oil, fruit seed oil (made from grape, black-currant, orange, or kiwi fruit seeds), colza, copra, groundnut, onager, palm, castor, linseed, jojoba, chia, and olive oils, cereal germ oils such as wheat germ oils, bran oil, rice oil, karite oil; acetylglycerides; octanoates, decanoates or ricinoleates of alcohols or of polyalcohols; triglycerides of fatty acids; glycerides; paraffin oil, Vaseline oil, perhydrosqualene; fatty alcohols (stearylic alcohol, cetylic alcohol) and fatty acids (stearic acid) and their esters; polyalkyl ($C_1$–$C_{20}$) siloxanes, and in particular those having trimethylsilyl terminal groups, preferably those whose viscosity is less than 0.06 $m^2$/s, among which mention can be made of linear polydimethylsiloxanes and alkylmethylpolysiloxanes such as cetyl dimethicone (CTFA name).

Mention can also be made of hydrocarbonated oils that are partially fluorinated, or perfluorinated oils, and in particular perfluoropolyethers and perfluoroalcanes.

The oily phase, i.e. the oil droplets dispersed in the layer of polymer, may be present in a proportion by weight relative to the total weight of the composition lying in the range 0.1% to 30%. Preferably, this percentage lies in the range 5% to 25%.

Alternatively, the liposoluble active ingredients are incorporated in a layer of hydrophobic polymer, in the form of powder or of granules.

In order to apply the adhesive matrix 3 onto the backing sheet 2 during manufacture, the backing sheet 2 is caused to advance, and the adhesive matrix 3, as in the solvent phase, is deposited by coating.

The solvent is then evaporated off.

It is advantageous for the backing sheet 2 in contact with the above-mentioned solvent not to be stretchable, at least in the direction in which it advances during coating, because this facilitates guiding it and winding it up.

The invention is not limited to the above-described embodiments, and, for example, it is possible to combine perforations and cutouts in the same backing sheet.

What is claimed is:

1. A mask for the face or the body, said mask comprising a backing sheet coated on one of its faces with an adhesive matrix containing a permanent adhesive, said adhesive matrix being capable of adhering prior to use both to dry skin and to wet skin, at least one of the backing sheet and the adhesive matrix containing at least one active ingredient serving to exert a specific action on the skin, wherein the adhesive matrix is stretchable at least in the wet state, in order to enable the mask to be adapted to fit the shape of the face or of the portion of the body to be treated, the backing sheet being chosen to be capable, at least in the wet state, of stretching so as to accompany the deformations in the adhesive matrix.

2. A mask for the face or body, wherein the mask comprises:

a backing sheet coated on one of its faces with an adhesive matrix containing a permanent adhesive that adheres both to dry and wet skin;

at least one of the backing sheet and the adhesive matrix containing at least one active ingredient serving to exert a specific action on the skin;

wherein the adhesive matrix is stretchable at least in the wet state, in order to enable the mask to be adapted to fit a shape of the face or a portion of the body to be treated;

the backing sheet being chosen to be capable, at least in the wet state, of stretching so as to accompany deformations in the adhesive matrix; and wherein, during use, the mask has an elongation factor in at least one direction that lies in a range of 5% to 30%.

3. A mask according to claim 1, wherein the adhesive matrix forms an occlusive layer.

4. A mask according to claim 1, wherein the backing sheet is provided with perforations and/or with cutouts.

5. A mask according to claim 1, containing one or more active ingredients that are water-soluble and/or liposoluble, and that are embedded in the adhesive matrix.

6. A mask according to claim 1, containing one or more water-absorbant substances embedded in the adhesive matrix.

7. A mask according to claim 1, wherein the backing sheet is made of a material that swells in water.

8. A mask according to claim 1, wherein the backing sheet is constituted by an elastic woven fabric.

9. A mask according to claim 1, wherein the backing sheet is constituted by a hydrophilic non-woven fabric.

10. A mask according to claim 1, wherein the backing sheet contains one or more water-absorbant fibers or particles or substances.

11. A mask according to claim 1, wherein the non-woven fabric contains a large proportion of viscose or of cotton.

12. A mask according to claim 1, wherein the adhesive and the backing sheet are chosen such that, one it is wet, the mask has a surface area in the stretched state that is greater by an amount in the range of 5% to 70% than the area of the mask in the dry state.

13. A mask according to claim 1, containing active ingredients chosen to exert an action selected from the group consisting of moistening, smoothing, lightening, toning up, slimming, healing, and anesthetizing.

14. A mask according to claim 1, wherein the backing sheet is not stretchable so long as it is not impregnated with water.

15. A method for treating a face or neck, comprising applying a mask as defined in claim 1 to the face or neck.

16. A method for treating thighs, comprising applying a mask as defined in claim 1 to the thighs.

17. A method for treating the face or body of a user, comprising immersing a mask as defined in claim 1 in water, and then applying the mask to the skin of the face or body by being stretched so as to be adapted to fit the morphology of the user.

18. A method for treating the face or body of a user, comprising applying a mask as defined in claim 1 in the dry state on wet skin, and then spraying the backing sheet with water.

19. A mask according to claim 2, wherein said elongation factor in at least one direction lies in the range 10% to 30%.

20. A mask according to claim 2, wherein said elongation factor in at least one direction lies in the range 15% to 30%.

21. A mask according to claim 6 wherein said water-absorbent substance is selected from the group consisting of polyacrylates, alginates, derivatives of corn or of cellulose and natural or synthetic water-absorbent fibers or particles.

22. A mask according to claim 11, wherein the non-woven fabric contains 30–90% by weight of viscose or cotton.

23. A mask according to claim 12, wherein said surface area in the stretched state is greater by an amount in the range of 10% to 70% than the area of the mask in the dry state.

24. A mask according to claim 12, wherein said surface area in the stretched state is greater by an amount in the range of 20% to 70% than the area of the mask in the dry state.

25. A mask according to claim 14, wherein the backing sheet is not stretchable when it is in contact with the matrix in the runny state, in solvent phase, during manufacture of the mask.

26. A mask for the face or body, wherein the mask comprises:
   a backing sheet coated on one of its faces with an adhesive matrix containing a permanent adhesive that adheres both to dry and wet skin;
   at least one of the backing sheet and the adhesive matrix containing at least one active ingredient serving to exert a specific action on the skin;
   wherein the adhesive matrix is stretchable at least in the wet state, in order to enable the mask to be adapted to fit a shape of the face or a portion of the body to be treated;
   the backing sheet being chosen to be capable, at least in the wet state, of stretching so as to accompany deformations in the adhesive matrix; and
   wherein the adhesive matrix is chosen such that, when it is applied in a runny state on the backing sheet during manufacture of the mask, it has viscosity preventing it from passing through said backing sheet.

27. A mask for the face or body, wherein the mask comprises:
   a backing sheet coated on one of its faces with an adhesive matrix containing a permanent adhesive that adheres both to dry and wet skin;
   at least one of the backing sheet and the adhesive matrix containing at least one active ingredient serving to exert a specific action on the skin;
   wherein the adhesive matrix is stretchable at least in the wet state, in order to enable the mask to be adapted to fit a shape of the face or a portion of the body to be treated;
   the backing sheet being chosen to be capable, at least in the wet state, of stretching so as to accompany the deformations in the adhesive matrix; and
   wherein the adhesive matrix is deposited in a quantity lying in a range of 15 g/m$^2$ to 70 g/m$^2$ on the backing sheet.

28. A mask for the face or body, wherein the mask comprises:
   a backing sheet coated on one of its faces with an adhesive matrix containing a permanent adhesive that adheres both to dry and wet skin;
   at least one of the backing sheet and the adhesive matrix containing at least one active ingredient serving to exert a specific action on the skin;
   wherein the adhesive matrix is stretchable at least in the wet state, in order to enable the mask to be adapted to fit a shape of the face or a portion of the body to be treated;
   the backing sheet being chosen to be capable, at least in the wet state, of stretching so as to accompany deformations in the adhesive matrix; and
   wherein the backing sheet contains polypropylene or polyester.

29. A mask according to claim 28, wherein the backing sheet contains polypropylene or polyester in a proportion in the range of 5% to 95% by weight.

30. A mask for the face or the body, said mask comprising a backing sheet coated on one of its faces with an adhesive matrix containing a permanent adhesive that adheres both to dry skin and to wet skin, at least one of the backing sheet and the adhesive matrix containing at least one active ingredient serving to exert a specific action on the skin, wherein the adhesive matrix is stretchable at least in the wet state, in order to enable the mask to be adapted to fit the shape of the face or of the portion of the body to be treated, the backing sheet being chosen to be capable, at least in the wet state, of stretching so as to accompany the deformations in the adhesive matrix, wherein the adhesive is hydrophobic.

31. A mask for the face or the body, said mask comprising a backing sheet coated on one of its faces with an adhesive matrix containing a permanent adhesive that adheres both to dry skin and to wet skin, at least one of the backing sheet and the adhesive matrix containing at least one active ingredient serving to exert a specific action on the skin, wherein the adhesive matrix is stretchable at least in the wet state, in order to enable the mask to be adapted to fit the shape of the face or of the portion of the body to be treated, the backing sheet being chosen to be capable, at least in the wet state, of stretching so as to accompany the deformations in the adhesive matrix, wherein the backing sheet is provided with diamond-shaped perforations.

32. A mask for the face or the body, said mask comprising a backing sheet coated on one of its faces with an adhesive matrix containing a permanent adhesive that adheres both to dry skin and to wet skin, at least one of the backing sheet and the adhesive matrix containing at least one active ingredient serving to exert a specific action on the skin, wherein the adhesive matrix is stretchable at least in the wet state, in order to enable the mask to be adapted to fit the shape of the face or of the portion of the body to be treated, the backing sheet being chosen to be capable, at least in the wet state, of stretching so as to accompany the deformations in the adhesive matrix, wherein the backing sheet is provided with slots disposed in staggered manner.

33. A mask for the face or the body, said mask comprising a backing sheet coated on one of its faces with an adhesive matrix containing a permanent adhesive that adheres both to dry skin and to wet skin, at least one of the backing sheet and the adhesive matrix containing at least one active ingredient serving to exert a specific action on the skin, wherein the adhesive matrix is stretchable at least in the wet state, in order to enable the mask to be adapted to fit the shape of the face or of the portion of the body to be treated, the backing sheet being chosen to be capable, at least in the wet state, of stretching so as to accompany the deformations in the adhesive matrix, wherein the adhesive is chosen from the following list: adhesives based on acrylic, vinyl, polyurethane, silicone, or elastomer, and copolymers and/or mixtures thereof.

* * * * *